(12) United States Patent
Heesch et al.

(10) Patent No.: US 8,671,941 B2
(45) Date of Patent: Mar. 18, 2014

(54) RESPIRATOR

(75) Inventors: Ralf Heesch, Lübeck (DE); Karsten Hoffmann, Kassendorf/Griebel (DE); Henryk Schnaars, Lübeck (DE); Ahmet Türker, Ratekau (DE)

(73) Assignee: Dräger Medical GmbH, Lübeck (DE)

( * ) Notice: Subject to any disclaimer, the term of this patent is extended or adjusted under 35 U.S.C. 154(b) by 374 days.

(21) Appl. No.: 12/953,673

(22) Filed: Nov. 24, 2010

(65) Prior Publication Data

US 2011/0146679 A1 Jun. 23, 2011

(30) Foreign Application Priority Data

Dec. 18, 2009 (DE) .......................... 10 2009 059 032

(51) Int. Cl.
*F24J 3/00* (2006.01)
(52) U.S. Cl.
USPC ..................................................... 128/204.17
(58) Field of Classification Search
USPC ............. 128/204.17, 203.26, 203.16, 200.24, 128/201.13, 203.17, 206.26, 203.27, 128/204.18, 204.21; 219/258, 530; 165/166
See application file for complete search history.

(56) References Cited

U.S. PATENT DOCUMENTS

| | | | | |
|---|---|---|---|---|
| 4,931,626 A * | 6/1990 | Shikama et al. | .............. | 219/540 |
| 5,259,370 A * | 11/1993 | Howe | ..................... | 128/200.14 |
| 6,059,025 A * | 5/2000 | Hossfeld | ...................... | 165/166 |
| 6,840,313 B2 * | 1/2005 | Abiko et al. | .................. | 165/166 |
| 7,610,701 B2 * | 11/2009 | Cavada | ............................. | 38/82 |
| 8,049,143 B2 * | 11/2011 | Andel et al. | ................ | 219/443.1 |
| 2003/0200968 A1 * | 10/2003 | Hoffmann et al. | ....... | 128/204.17 |
| 2005/0248045 A1 * | 11/2005 | Anthony | ....................... | 261/154 |
| 2007/0221366 A1 * | 9/2007 | Murayama et al. | ........... | 165/166 |
| 2008/0066751 A1 * | 3/2008 | Polacsek | .................. | 128/204.17 |
| 2009/0056715 A1 * | 3/2009 | Cortez et al. | ............. | 128/203.26 |
| 2009/0090363 A1 * | 4/2009 | Niland et al. | ............ | 128/203.26 |

FOREIGN PATENT DOCUMENTS

| | | |
|---|---|---|
| AT | 107 900 B | 11/1927 |
| CN | 101 220 988 A | 7/2008 |
| DE | 36 18 614 A1 | 12/1987 |
| DE | 3629353 * | 7/1988 |
| DE | 10219286 | 7/2003 |

OTHER PUBLICATIONS http://www.epo.org/searching/free/espacenet.html 2013 Machine Translation of DE3629353.*

* cited by examiner

*Primary Examiner* — Loan Thanh
*Assistant Examiner* — Nyca T Nguyen
(74) *Attorney, Agent, or Firm* — McGlew and Tuttle, P.C.

(57) ABSTRACT

A respirator with a breathing gas block (2) and with breathing gas ducts (13, 15, 17) and with a heater has the electric components located outside of the breathing gas-carrying areas. A heated distributor plate is flatly in contact on the underside of the breathing gas block (2) and has heating ribs (21, 22) that are in contact with breathing gas ducts (13, 15) at least in some areas.

18 Claims, 2 Drawing Sheets

RESPIRATOR

CROSS REFERENCE TO RELATED APPLICATIONS

This application claims the benefit of priority under 35 U.S.C. §119 of German Patent Application DE 10 2009 059 032.3 filed Dec. 18, 2009, the entire contents of which are incorporated herein by reference.

FIELD OF THE INVENTION

The present invention pertains to a respirator (also known as a ventilator) with a breathing gas block with a cover which define breathing gas ducts as well as with a heater.

BACKGROUND OF THE INVENTION

A respirator of the type mentioned is known from DE 102 19 286 C1. The prior-art respirator comprises a breathing gas block, which is provided with a plurality of breathing gas ducts, through which the breathing gas is sent. A carbon dioxide absorber, which binds the carbon dioxide expired by the patient, is located below the breathing gas block. A metallic valve plate with a heating foil and a cover are arranged above the breathing gas block in a sandwich pattern. To avoid condensation effects within the respirator, the valve plate located centrally is heated by the heating foil, said heating foil being arranged flat at the points that are especially prone to water vapor condensation.

Even though the guiding of the heat flux within the respirator can be readily set by the centrally located valve plate, around which the breathing gas flows, the three-layer structure of the respirator is highly cost-intensive and the electric contacting of the heating foil requires a plug-type connection, which is led to the outside. Since the respirator must be taken apart for cleaning purposes, a plurality of components, which must be processed one by one, are present due to the three-layer design. There is a risk in this connection that the exposed heating foil will be damaged during cleaning or the electric contacts will corrode. In addition, the centrally located valve plate requires sealing against both the cover and the breathing gas block.

SUMMARY OF THE INVENTION

The basic object of the present invention is to improve a respirator of the type mentioned such that while heat conduction within the breathing gas ducts is provided (which is good), electric components are arranged in a protected manner, and to provide a process for heating a respirator.

According to the invention, a respirator is provided containing a breathing gas block with a cover. The cover and the block define breathing gas ducts. A heater is provided which comprises a heated distributor plate, which is flatly in contact on the underside of the breathing gas block and is formed of a material with good thermal conductivity. The heated distributor plate has heating ribs that are in contact with breathing gas ducts at least in some areas.

The heating element may be attached as a first heating element to the distributor plate by means of a metallic heat distributor plate of a flat design. Two heating elements may be attached to the heat distributor plate in such a way that a second heating element is arranged in the area of an inspiration duct passing through inspiration gas. The heated distributor plate may be provided with perforations, areas of thicker material or holes in the material for deflecting (directing/routing) the heat transport.

The breathing gas block may have vertically extending convection ducts for heat balancing. The breathing gas block may be surrounded by an insulating housing.

The advantage of the device according to the present invention can be seen in that a heated distributor plate, which is flatly in contact, is formed of a material with good thermal conductivity and has heating ribs that are in contact with the breathing gas ducts in at least some areas, is arranged on the underside of the breathing gas block. The heat flux can be distributed by the distributor plate over the breathing gas block, and areas prone to condensation, which are in contact with the breathing gas ducts, can be heated in a specific manner. The heat supply to the breathing gas ducts can be specifically controlled by selecting the number and cross-sectional area of the heating ribs. The heating ribs are designed such that they come into contact with the breathing gas ducts.

The heat is advantageously supplied to the distributor plate by means of a flat, metallic heat distributor plate, to which a heating element is attached. The heat distributor plate assumes a heat-distributing function in such a manner that heat fed locally via the heating element is uniformly distributed.

Instead of an individual heating element, a plurality of heating elements may be present as well in order to concentrate the heat output to certain parts of the surface or to feed an exactly dosed heat output to other parts of the surface. It is especially advantageous in this case to arrange one of the heating elements in the area of a breathing gas-carrying inspiration gas duct and to provide it with a separate control loop for setting the heat output. As a result, the inspiration gas can be adjusted to a predetermined gas temperature.

The distributor plate is advantageously provided with perforations, areas with thicker material or holes in the material in order to locally intensify or also to reduce the heat flux. The heat flux can be guided as a result in a specific manner into areas in which a high thermal output is needed, or it is also possible to supply other areas with a lower heat output. The heat flux can be guided around certain areas by means of individual perforations in the distributor plate. The areas with thicker material are used to intensify the heat flux in certain areas, whereas holes in the material serve the purpose of reducing the heat flux. The heat from the distributor plate increases upwardly in the areas of increased heat flux and it also heats the areas located above it.

The heat distributor plate, which is located under the distributor plate, is likewise provided in some areas with perforations for deflecting the heat flux. The perforations may be round, angular or free-form perforations and combined with one another in various embodiments.

The respirator is advantageously surrounded by an insulating housing with a protective cover, with which the release of heat of the respirator to the environment or also to a device mount surrounding the respirator is minimized. In addition, the heat output to be supplied via the heating elements is reduced by the insulating housing. Individual convection ducts, through which heat can rise upward in the direction of the protective cover, are present within the breathing gas block. A heat cushion, by which the heat loss of the respirator is further reduced, is formed under the protective cover due to the convention ducts.

The process according to the present invention pertains to the heating of a respirator, which has breathing gas ducts in a breathing gas block. The process steps include arranging a heated distributor plate, which is flatly in contact and is made of a material with good thermal conductivity, on the underside of the breathing gas block and providing at this distributor plate heating ribs, which are in contact at least with individual breathing gas ducts.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
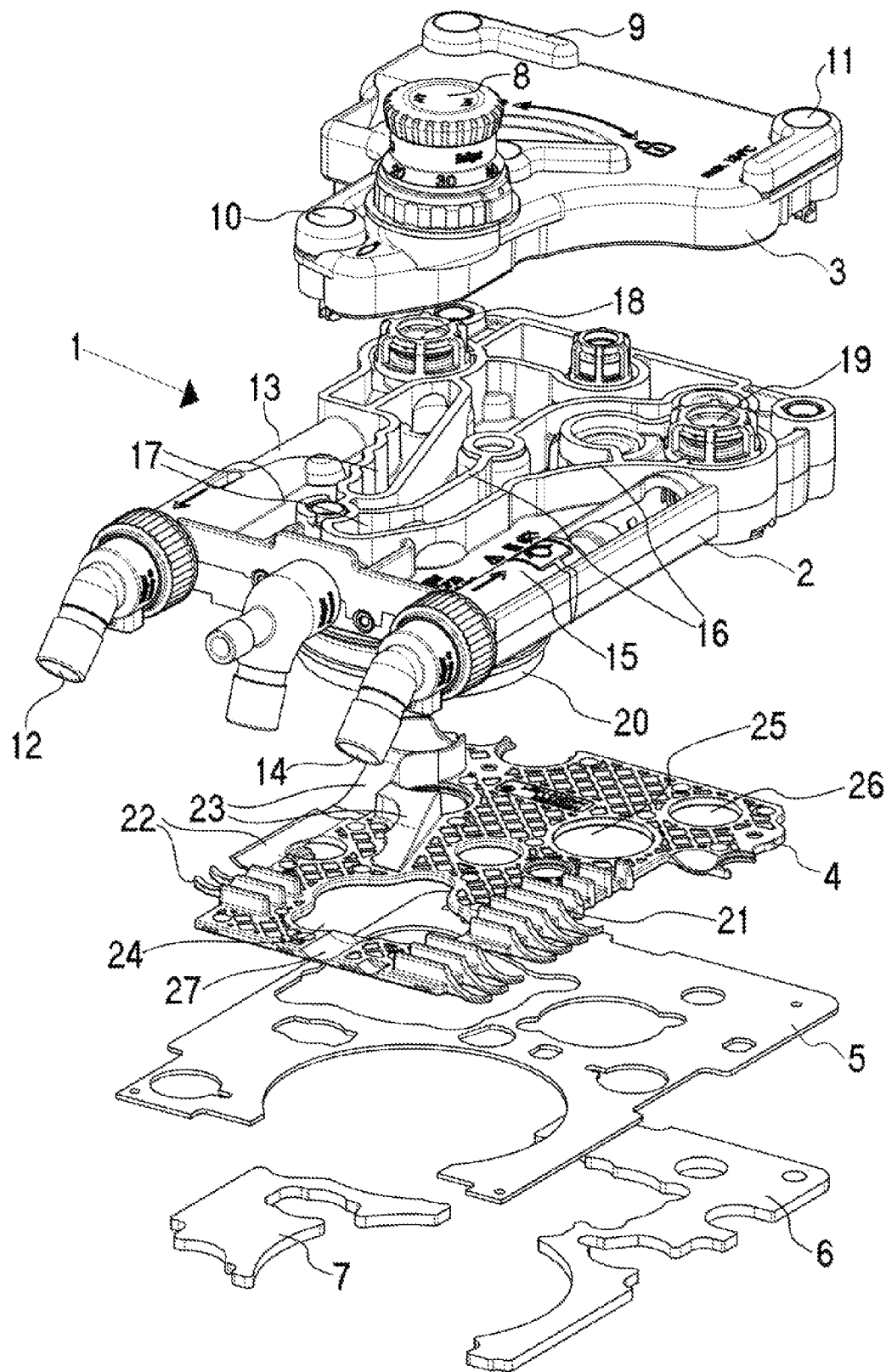
FIG. 1 is a perspective view of a respirator.

Referring to the drawings in particular, FIG. 1 schematically shows the design of a respirator 1 according to the present invention in a perspective view. Respirator 1 comprises a breathing gas block 2 with a detachable cover 3 on the top side and with a heated distributor plate 4 on the underside, which is flatly in contact at a heat distributor plate 5 with a first heating element 6 and with a second heating element 7.

Cover 3 contains an adjustable pressure relief valve 8 and three locking levers 9, 10, 11, with which cover 3 can be braced against the breathing gas block 2.

The breathing gas block 2 contains an inspiration port 12 at an inspiration breathing gas duct 13 and an expiration port 14 at an expiration breathing gas duct 15. Individual partitions 16 within the breathing gas block 2 form further breathing gas ducts 17. Directional valves 18, 19 are used to guide the breathing gas flow within the breathing gas block 2 from the expiration port 14 to the inspiration port 12. A port adapter 20 for a carbon dioxide absorber, not shown more specifically, is arranged under the breathing gas block 2.

The distributor plate 4 located under the breathing gas block 2 is designed such that the heat flux can be directed specifically to intended areas of the breathing gas block 2. First heating ribs 21 are provided for this, which are in contact with the wall of the expiration breathing gas duct 15 and heat same. The expiration breathing gas duct 15 is arranged such that it directly joins the expiration port 14. A flow sensor, not shown more specifically in FIG. 1, is located at the end of the expiration breathing gas duct 15. Condensation effects in the flow sensor are prevented from occurring due to the heating of the expired gas in the expiration breathing gas duct 15 on the incoming flow side of the flow sensor.

Second heating ribs 22 are located in the area of the inspiration breathing gas duct 13 and heat the inspiration gas. Areas with thicker material 23 are provided at the points at which increased heat output is needed. Perforations 24, 25, 26 of different designs are used to deflect the heat flux. A hole in the material 27 on the front side of the distributor plate 4 serves the purpose of reducing the heat flux between the first heating ribs 21 and the second heating ribs 22. The second heating ribs 22 facing the inspiration breathing gas duct 13 will thus be prevented from being heated by the first heating ribs 21.

The heat distributor plate 5 located under the distributor plate 4 preferably consists of aluminum, and other metals or ceramics are also suitable, which possess good heat conduction properties and low heat capacity. A material with low heat capacity makes it possible to rapidly regulate the temperature of the system. The first heating element 6 located under the heat distributor plate 5 heats the area around the expiration duct 15 and the middle area of the breathing gas block 2, while the second heating element 7 is associated with the inspiration duct 13. The heat distributor plate 5 and the distributor plate 4 are arranged in the installed position at closely spaced locations from one another and are ideally directly one on top of another.

Figure 2:
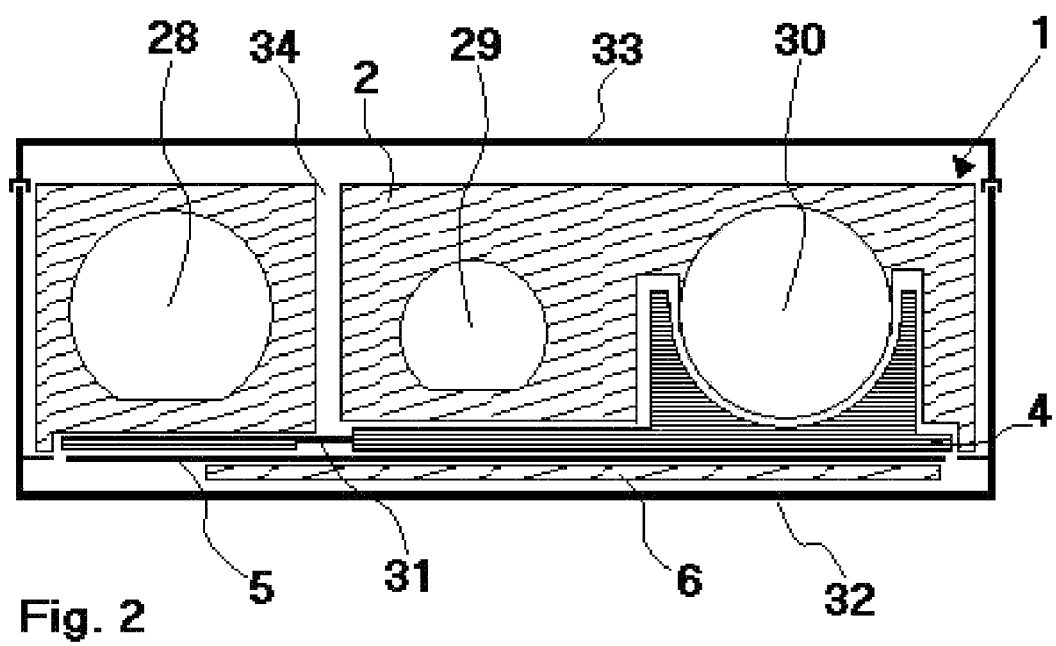
FIG. 2 is a cross-sectional individual gas ducts of the respirator according to FIG. 1.

FIG. 2 schematically shows three breathing gas ducts 28, 29, 30 within the breathing gas block 2 of the respirator 1, which are heated via the distributor plate 4 to different extents. The heat distributor plate 5 with the first heating element 6 is located under the distributor plate 4.

A first breathing gas duct 30 needs a higher heat output, so that the distributor plate 4 is designed there such that it completely surrounds the first breathing gas duct 30, so that more heat-radiating surface is available. Due to its thin wall thickness, the first breathing gas duct 30 is designed on its underside such that the heat is sent directly inside via the distributor plate 4.

A second breathing gas duct 29 is heated less, because the distributor plate 4 is located at a greater distance from the second breathing gas duct 29 than the first breathing gas duct 30. The release of heat is further reduced at the third breathing gas duct 28 by a hole in the material 31, which reduces the heat flux within the distributor plate 4 to the third breathing gas duct 28.

The respirator 1 is surrounded by an insulating housing 32 with a protective cover 33, with which the release of heat of the respirator 1 to the environment or even to a device mount, which surrounds the respirator 1 and is not shown more specifically, will be minimized. In addition, the heat output to be fed via the heating element 6, 7 decreases due to the insulating housing. Individual convection ducts 34, only one of which is shown as an example in FIG. 2, and through which the heat can rise up in the direction of the protective cover 33, are present within the breathing gas block 2. A heat cushion, by which the heat loss of the respirator 1 is further reduced, is formed by the convection ducts 34 under the protective cover 33. Cover 3, FIG. 1, is not shown in FIG. 2 for the sake of greater clarity. Insulating housing 32 and protective cover 33 preferably consist of a plastic with low thermal conductivity.

While specific embodiments of the invention have been described in detail to illustrate the application of the principles of the invention, it will be understood that the invention may be embodied otherwise without departing from such principles.

APPENDIX

List of Reference Numbers

1 Respirator
2 Breathing gas block
3 Cover
4 Distributor plate
5 Heal distributor plaie
6 First healing clement
7 Second heating clement
8 Pressure relief valve
9, 10, 11 Locking lever
12 Inspiration port
13 Inspiration duct
14 Expiration port 15 Expiration duct
16 Partition
17 Breathing gas duct
18, 19 Directional valve
20 Port adapter
21 First heating ribs
22 Second heating ribs
23 Area with thicker material
24, 25, 26 Perforation
27, 31 Hole in material
28, 29, 30 Breathing gas duel
32 Insulating housing
33 Protective cover
34 Convection duct

What is claimed is:

1. A respirator comprising:
a breathing gas block;
a cover, at least one or both of said breathing gas block and said cover defining breathing gas ducts, each of said breathing gas ducts having an outer surface; and
a heater comprising a heated distributor plate flatly in contact with the breathing gas block on an underside of the breathing gas block, said heater being formed of a material with good thermal conductivity and including heating ribs in contact with portions of said outer surface of each of said breathing gas ducts, wherein the heater further comprises a heating element providing a heat output in thermal contact with said distributor plate.

2. A respirator in accordance with claim 1, wherein the heater further comprises:
a metallic heat distributor plate of a flat design, said heating element being attached to said distributor plate by said metallic heat distributor plate.

3. A respirator in accordance with claim 2, wherein said heater further comprises another heating element wherein said heating element and said another heating element provide two heating elements in thermal contact with said distributor plate by said metallic heat distributor plate wherein said another heating element is arranged in an area of one of said breathing gas ducts in a form of an inspiration duct passing through inspiration gas.

4. A respirator in accordance with claim 3, wherein the metallic heat distributor plate is provided with perforations and includes areas of thicker material or holes in the material for deflecting heat transport.

5. A respirator in accordance with claim 4, wherein the breathing gas block has vertically extending convection ducts for heat balancing.

6. A respirator in accordance with claim 1, further comprising an insulating housing wherein said breathing gas block is surrounded by said insulating housing.

7. A process for heating a respirator, the process comprising the steps of:
providing a breathing gas block;
providing a cover;
connecting the breathing gas block and the cover to define breathing gas ducts provided as part of an assembly of said breathing gas block and said cover;
providing a heater comprising a heated distributor plate made of a material with good thermal conductivity and with heating ribs;
arranging the heated distributor plate flatly in contact with the breathing gas block on an underside of the breathing gas block; and
providing the heating ribs in contact with outer surface portions of individual breathing gas ducts, wherein the heater further comprises a heating element providing a heat output in thermal contact with said distributor plate.

8. A process in accordance with claim 7, wherein the heater further comprises:
a metallic heat distributor plate of a flat design and further comprising the step of:
attaching the heating element to the heated distributor plate by the metallic heat distributor plate.

9. A process in accordance with claim 8, wherein the heater further comprises:
another heating element and further comprising the step of:
arranging the another heating element in an area of one of the breathing gas ducts in a form of an inspiration duct passing through inspiration gas.

10. A process in accordance with claim 9, further comprising:
deflecting heat transport from the heater by providing the heated distributor plate with perforations and areas of thicker material or holes.

11. A process in accordance with claim 10, wherein the breathing gas block has vertically extending convection ducts for heat balancing.

12. A process in accordance with claim 7, wherein the breathing gas block is surrounded by an insulating housing.

13. A respirator comprising:
a breathing gas block;
a cover, one or both of said breathing gas block and said cover defining breathing gas ducts, said breathing gas ducts having outer surfaces formed by an outer surface of said breathing gas block; and
a heater comprising a heated distributor plate in contact with the breathing gas block on an underside of the breathing gas block, said heater being formed of a thermally conductive material and including a plurality of heating ribs with a contact contour shaped corresponding to portions of said an outer surface of said breathing gas block, each contact contour being in contact with one of said outer surfaces of said breathing gas ducts, wherein the heater further comprises a heating element providing a heat output in thermal contact with said distributor plate.

14. A respirator in accordance with claim 13, wherein the heater further comprises:
a metallic heat distributor plate of a flat design, said heating element being attached to said heated distributor plate by said metallic heat distributor plate.

15. A respirator in accordance with claim 14, wherein said heater further comprises another heating element to provide two heating elements attached to the metallic heat distributor plate wherein said another heating element is arranged in an area of one of said breathing gas ducts in a form of an inspiration duct for passing through inspiration gas.

16. A respirator in accordance with claim 15, wherein the heated distributor plate is provided with perforations and includes areas of thicker material or holes in the material for deflecting heat transport.

17. A respirator in accordance with claim 16, wherein the breathing gas block has vertically extending convection ducts.

18. A respirator in accordance with claim 13, further comprising an insulating housing wherein the breathing gas block is surrounded by said insulating housing.

* * * * *